(12) United States Patent
Bradley (10) Patent No.: US 8,661,896 B2
(45) Date of Patent: Mar. 4, 2014

(54) PROTECTIVE ENCLOSURE FOR USE WITH A SENSOR FOR DETECTING AN ANALYTE

(75) Inventor: Michael Kevin Bradley, Irwin, PA (US)

(73) Assignee: Mine Safety Appliances Company, Cranberry Township, PA (US)

( * ) Notice: Subject to any disclaimer, the term of this patent is extended or adjusted under 35 U.S.C. 154(b) by 37 days.

(21) Appl. No.: 13/190,813

(22) Filed: Jul. 26, 2011

(65) Prior Publication Data

US 2013/0025367 A1  Jan. 31, 2013

(51) Int. Cl.
| | |
|---|---|
| *G01D 11/24* | (2006.01) |
| *G01L 19/14* | (2006.01) |
| *G01P 1/02* | (2006.01) |
| *B21D 39/03* | (2006.01) |
| *B23P 11/00* | (2006.01) |
| *G01J 5/02* | (2006.01) |

(52) U.S. Cl.
USPC ............................... 73/431; 29/428; 250/343

(58) Field of Classification Search
USPC ............................... 73/431; 29/428; 250/343
See application file for complete search history.

(56) References Cited

U.S. PATENT DOCUMENTS

| 6,075,246 | A | 6/2000 | Stock | |
|---|---|---|---|---|
| 7,178,381 | B2 * | 2/2007 | Tajima et al. | 73/31.02 |
| 7,405,827 | B2 * | 7/2008 | Keranen | 356/432 |
| 7,928,394 | B1 * | 4/2011 | Richer | 250/343 |
| 2002/0139934 | A1 * | 10/2002 | Chang | 250/343 |
| 2003/0052792 | A1 * | 3/2003 | Koyano et al. | 340/632 |
| 2007/0089481 | A1 * | 4/2007 | Wansing | 73/23.2 |
| 2008/0277586 | A1 * | 11/2008 | Cardinale | 250/339.13 |
| 2009/0260445 | A1 * | 10/2009 | Kopp | 73/706 |
| 2012/0239313 | A1 * | 9/2012 | Champredonde et al. | 702/50 |

FOREIGN PATENT DOCUMENTS

| DE | 10226986 B4 | 1/2004 |
|---|---|---|
| KR | 20090008600 | 1/2009 |
| WO | WO2006030059 A1 | 3/2006 |
| WO | WO2013016323 A1 | 1/2013 |

* cited by examiner

*Primary Examiner* — Lisa Caputo
*Assistant Examiner* — Jamel Williams
(74) *Attorney, Agent, or Firm* — Bartony & Associates, LLC (57) ABSTRACT

A method of protecting a sensor for use in an environment, includes providing a protective enclosure formed in a plurality of sections, at least a first section of the plurality of sections being movable relative to a second section of the plurality of sections so that the protective enclosure can be placed around at least a portion of the sensor; placing the first section adjacent the sensor while the first section and the second section are in an open state; and moving the second section to place the first section and the second section in a closed state in which the first section and the second section encompass the at least a portion of the sensor.

19 Claims, 7 Drawing Sheets

PROTECTIVE ENCLOSURE FOR USE WITH A SENSOR FOR DETECTING AN ANALYTE

BACKGROUND

The following information is provided to assist the reader to understand the technology described below and certain environments in which such technology can be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

Protective enclosures or guards are often used with sensors such as infrared (IR) gas sensors to protect the sensors from undesirable elements (for example, dust, dirt, moisture etc.) in the environment in which the sensor is used. Among other things, such protective enclosures or guards protect the analytical volume from the inflow of water, as a result of rain, wind, waves etc. It is desirable that the protective enclosure protect the sensor from undesirable elements in the environment while allowing for quick transfer of the measured gas from that environment to the analytical volume of the sensor.

In the case of many currently available protective enclosures or guards used in connection with gas sensors, the enclosure must be oriented in a preferred direction to achieve both optimal response time and water rejection. Proper orientation is typically achieved in such currently available protective enclosures by either built-in constraints on the sensor housing or through manual orientation by the user. As a result, the protective enclosure is typically fixed. Response time and/or water rejection are negatively impacted in a substantial manner if the protective enclosure deviates from its optimal orientation.

Regardless of the orientation of currently available enclosures, most such enclosures have a negative effect upon response time as a result of relatively large internal volumes encompassing the sensor.

SUMMARY

In one aspect, a method of protecting a sensor for use in an environment includes providing a protective enclosure formed in a plurality of sections, at least a first section of the plurality of sections being movable relative to a second section of the plurality of sections so that the protective enclosure can be placed around at least a portion of the sensor; placing the first section adjacent the sensor while the first section and the second section are in an open state; and moving the second section to place the first section and the second section in a closed state in which the first section and the second section encompass the at least a portion of the sensor.

The second section can, for example, be movable relative to the first section to enclose at least a portion of the sensor including an analytical volume of the sensor within an internal volume of the protective enclosure. The protective enclosure can further include at least a first opening in the first section via which an analyte gas can enter the internal volume and an indirect pathway between the first opening and the internal volume.

The first section can, for example, be moveably connected to the second section via at least one hinged connection.

The first section can, for example, include a first outer portion and a first inner portion. The second section can, for example, include a second outer portion and a second inner portion.

The indirect pathway between the first opening and the internal volume can, for example, be created by at least one barrier member extending from a first outer portion of the first section and at least one barrier member extending from a first inner portion of the first section.

The protective enclosure can further include at least a second opening in the second section via which an analyte gas can enter the internal volume and an indirect pathway between the second opening and the internal volume. The indirect pathway between the second opening and the internal volume can, for example, be created by at least one barrier member extending from the second outer portion and at least one barrier member extending from the second inner portion.

A minimum cross-sectional area of the internal volume can, for example, be less than a cross sectional area of a component of the sensor encompassed by the protective enclosure.

The sensor can, for example, be an infrared sensor comprising a mirror support to which at least one mirror is attached. At least one of the first inner portion and the second inner portion can include a seating to seat the mirror support.

In another aspect, a system, includes a sensor and a protective enclosure removably attachable to at least a portion of the sensor. The protective enclosure includes a plurality of sections. At least a first section of the plurality of sections is movable relative to a second section of the plurality of sections.

The second section can, for example, be movable relative to the first section to enclose at least a portion of the sensor including an analytical volume of the sensor within an internal volume of the protective enclosure. The protective enclosure can, for example, further include at least a first opening in the first section via which an analyte gas can enter the internal volume and an indirect pathway between the first opening and the internal volume. The first section can, for example, be moveably connected to the second section via at least one hinged connection.

The first section can, for example, include a first outer portion and a first inner portion, and the second section can, for example, include a second outer portion and a second inner portion.

The indirect pathway between the first opening and the internal volume can, for example, be created by at least one barrier member extending from the first outer portion and at least one barrier member extending from the first inner portion.

The system can, for example, further include at least a second opening in the second section via which an analyte gas can enter the internal volume and an indirect pathway between the second opening and the internal volume. The indirect pathway between the second opening and the internal volume can, for example, be created by at least one barrier member extending from the second outer portion and at least one barrier member extending from the second inner portion.

A minimum cross-sectional area of the internal volume can, for example, be less than the cross sectional area of a component (for example, a mirror support or a mirror system) of the sensor encompassed by the protective enclosure.

The sensor can, for example, be an infrared sensor including a mirror support to which at least one mirror is attached. At least one of the first inner portion and the second inner portion can include a seating to seat the mirror support.

In a further aspect, a protective enclosure for use in connection with a sensor includes a first section, a second section movable relative to the first section to enclose at least a portion of the sensor comprising an analytical volume of the sensor within an internal volume of the protective enclosure, at least a first opening in the first section via which an analyte gas can enter the internal volume, and an indirect pathway between the first opening and the internal volume. As described above, the first section can, for example, be moveably connected to the second section via at least one hinged connection.

The technology described herein, along with the attributes and attendant advantages thereof, will best be appreciated and understood in view of the following detailed description taken in conjunction with the accompanying drawings.

DETAILED DESCRIPTION

As used herein and in the appended claims, the singular forms "a," "an", and "the" include plural references unless the content clearly dictates otherwise. Thus, for example, reference to "a section" includes a plurality of such sections and equivalents thereof known to those skilled in the art, and so forth, and reference to "the section" is a reference to one or more such sections and equivalents thereof known to those skilled in the art, and so forth.

FIGS. 1 through 16 illustrate a representative embodiment of a protective enclosure or environmental guard 100 to protect or guard an analytical volume 310 and/or components of a sensor 300 (see FIGS. 11 through 16) from the inflow of water, dirt etc. from the environment in which sensor 300 is used to sense or measure the concentration of an analyte, while allowing for quick transfer of the analyte gas to be measured.

Unlike currently available protective enclosures for use in connection with sensors, protective enclosure 100 is formed in a plurality of moveable sections. At least one of the sections is movable relative to at least one other section to enable placement of sensor 300 in operative connection with protective enclosure 100 while the sections of protective enclosure 100 are in an open state and subsequent closure of the sections (to a closed state) to enclose or encompass at least a portion of sensor 300 (or another sensor). In the representative embodiment illustrated in FIGS. 1 through 16, protective enclosure 100 includes two sections 110a and 110b which are movably (for example, pivotably or hingedly) connected to place protective enclosure 100 in an open state in which sensor 300 can be placed in operative connection with protective enclosure 100 as, for example, illustrated in FIGS. 11 and 12. As, for example, illustrated in FIG. 12, sensor 300 can first be placed adjacent to or seated within, for example, section 110a. Sections 110a and 110b can then be moved relative to each other to encompass or enclose at least a portion of sensor 300 as, for example, illustrated in FIG. 13.

Figure 1:
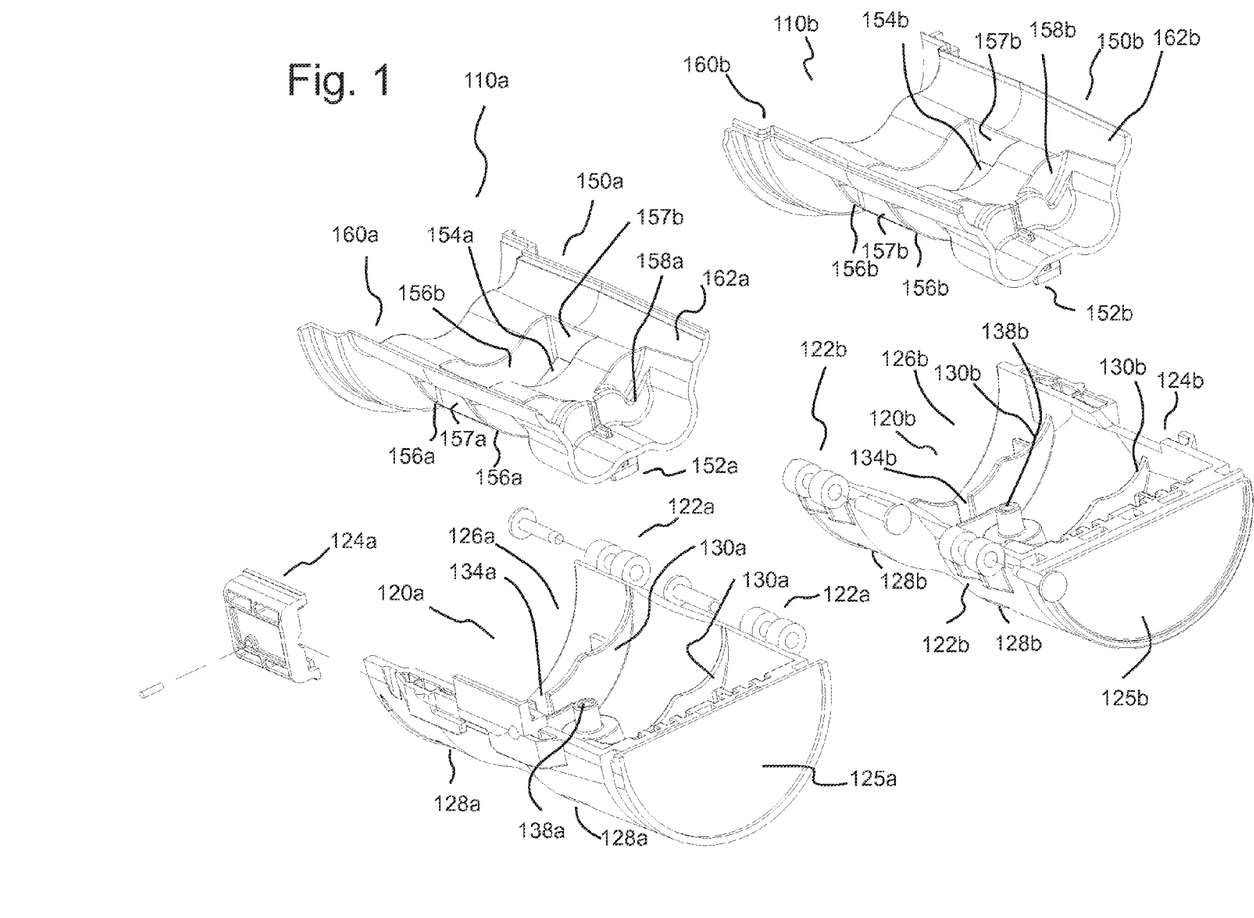
FIG. 1 illustrates a perspective, disassembled or exploded view of an embodiment of a protective enclosure for use in connection with a sensor such as an infrared gas sensor.

As illustrated, for example, in FIG. 1 first section 110a includes an outer portion 120a and an inner portion 150a. In a number of embodiments, outer portion 120a and inner portion 150a can, for example, be formed from one or more metals and/or one or more polymeric materials such as a polycarbonate/acrylonitrile butadiene styrene (ABS) alloy including a polymeric additive to provide anti-static properties, which can, for example, be connected via a snap or friction fit, via sonic welding, via adhesives, etc. Similarly, second section 110b includes an outer portion 120b and an inner portion 150b. Like first section 110a, outer portion 120b and inner portion 150b of second section 110b can, for example, be formed from one or more metals and/or one or more polymeric materials such as described above. In the illustrated embodiment, inner portions 150a and 150b, include extending sections 152a and 152b, respectively, which form a cooperating connection (for example, via a snap fit, a vibration weld, etc.) with cooperating seating 126a (not shown) and 126b (see FIG. 2). In a number of aspects, although not entirely, first section 110a and second section 110b were formed identically.

First section 110a and second section 110b can, for example, be movably connected via one or more cooperating hinge element 122a and 122b on outer portions 120a and 120b, respectively. A closure or locking mechanism 124a can for example, be provided on first section 120a, which cooperates with a cooperating closure or locking mechanism 124b on second section 120a to releasably maintain protective enclosure 100 in a closed state. Outer portions 120a and 120b include end caps or closures 125a and 125b, respectively, on a distal end thereof. Outer portions 120a and 120b further include openings 126a and 126b on an opposite or proximal end thereof.

Figure 2:
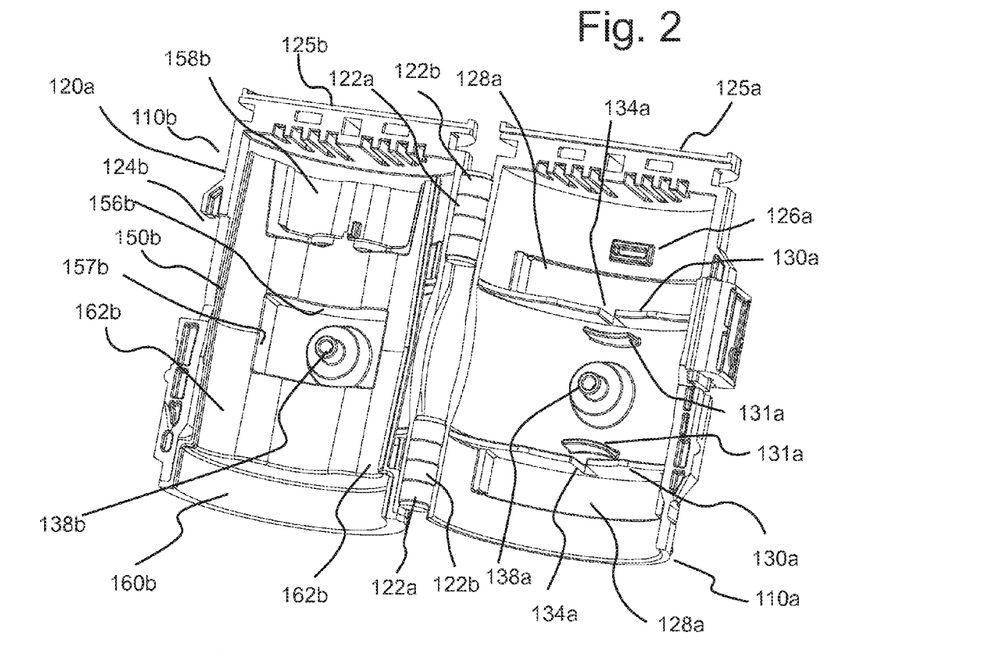
FIG. 2 illustrates a perspective, partially disassembled view of the protective enclosure of FIG. 1 in which an inner portion of the protective closure on the right hand side of the illustration is excluded.
Figure 3:
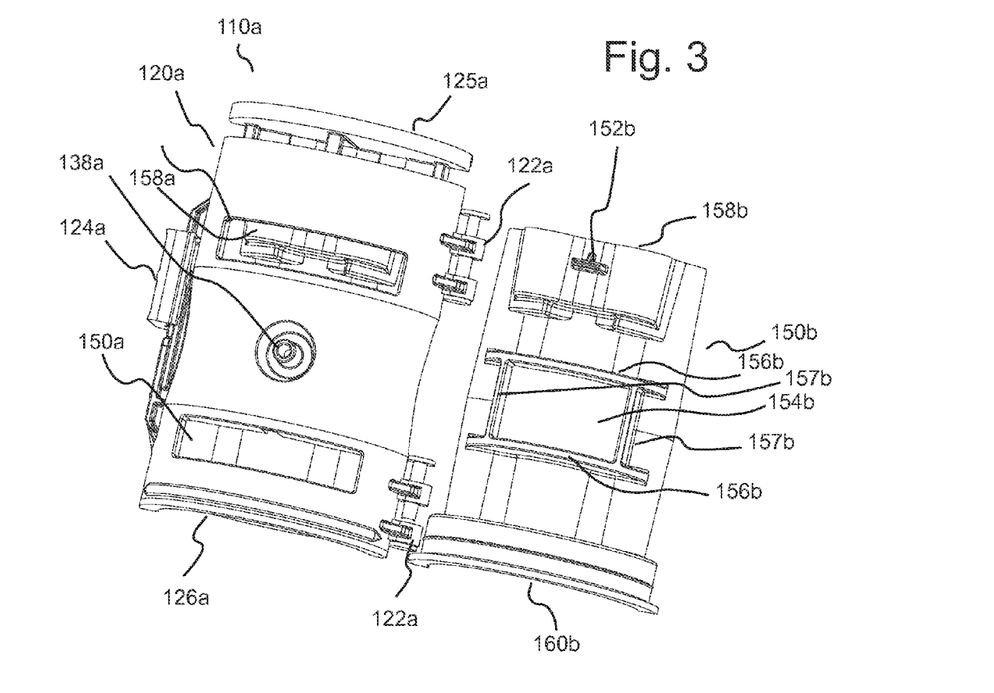
FIG. 3 illustrates another perspective, partially disassembled view of the protective enclosure of FIG. 1 in which an outer portion of the protective enclosure on the right hand side of the illustration is excluded.
Figure 4:
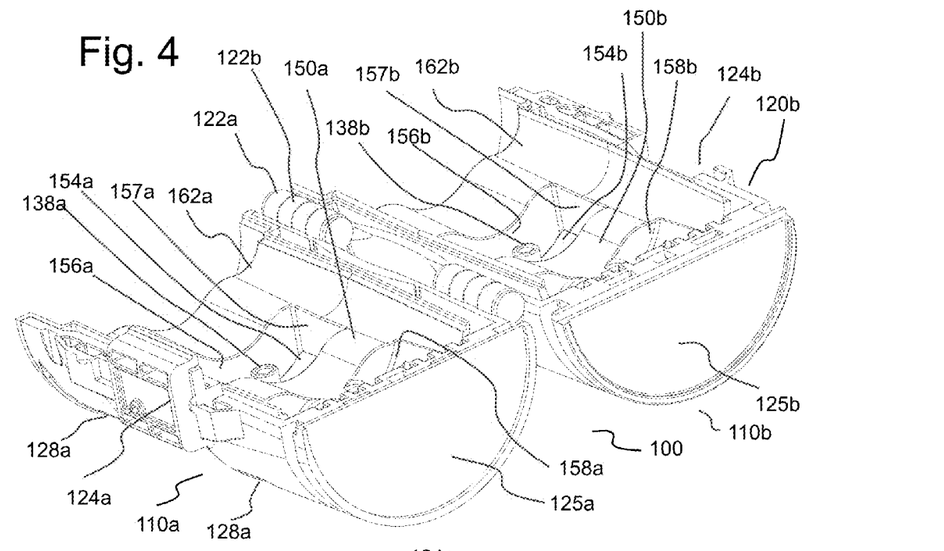
FIG. 4 illustrates perspective view of the protective enclosure of FIG. 1 in an open state.
Figure 5:
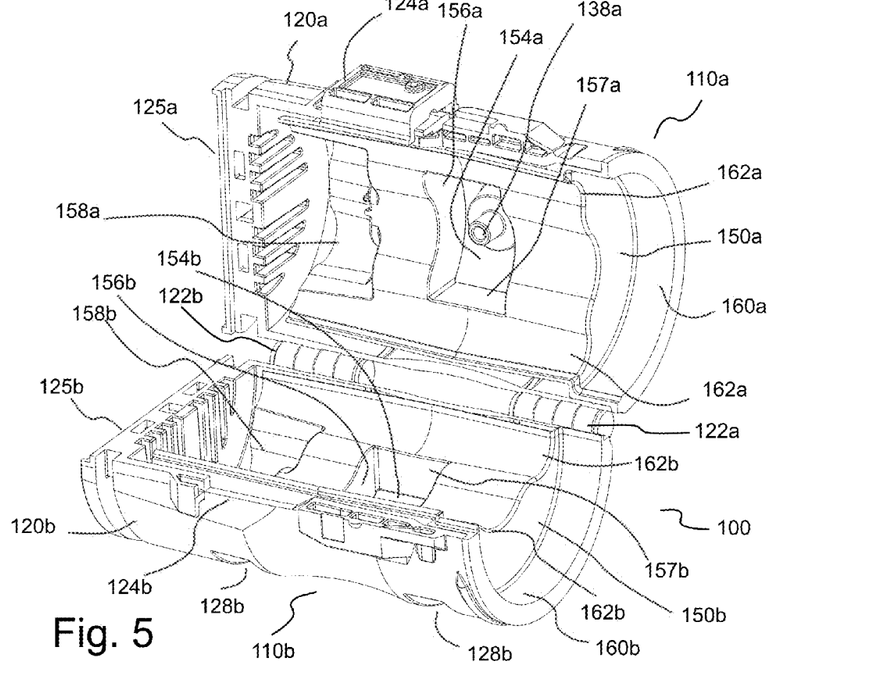
FIG. 5 illustrates another perspective view of the protective enclosure of FIG. 1 in an open state.
Figure 6:
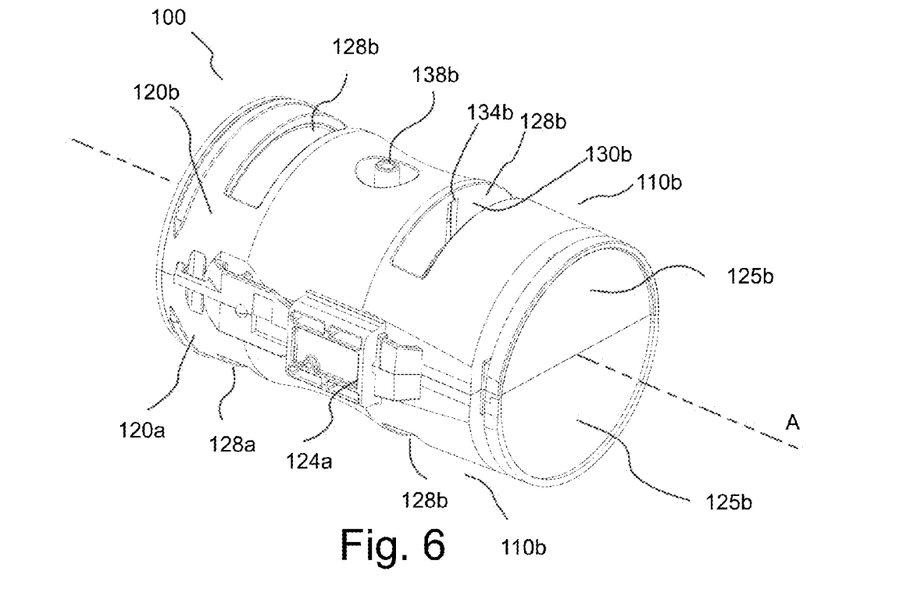
FIG. 6 illustrates a perspective view of the protective enclosure of FIG. 1 in a closed state.
Figure 7:
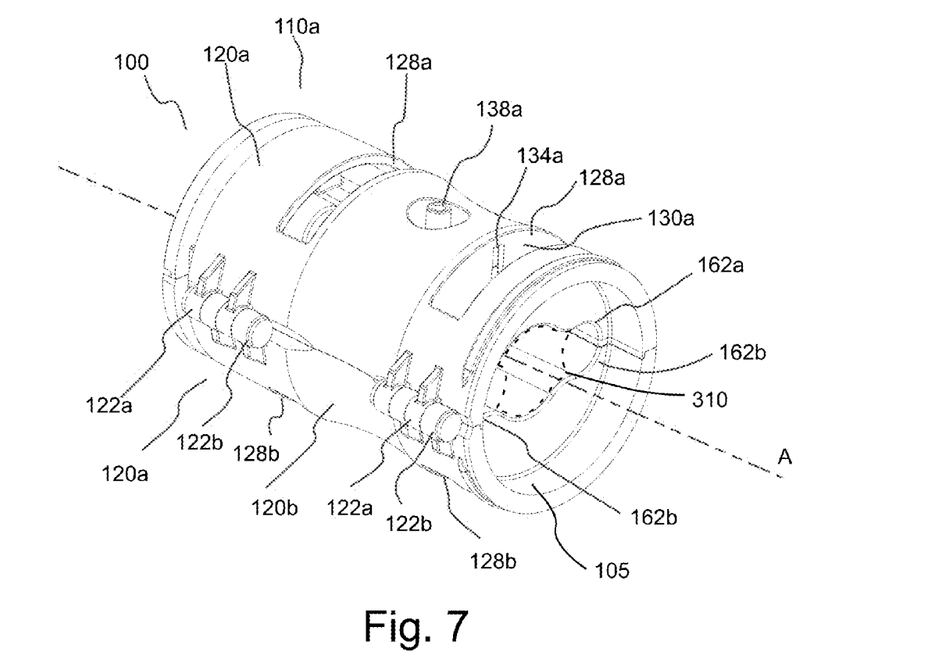
FIG. 7 illustrates another perspective view of the protective enclosure of FIG. 1 in a closed state.
Figures 8, 9, 10:
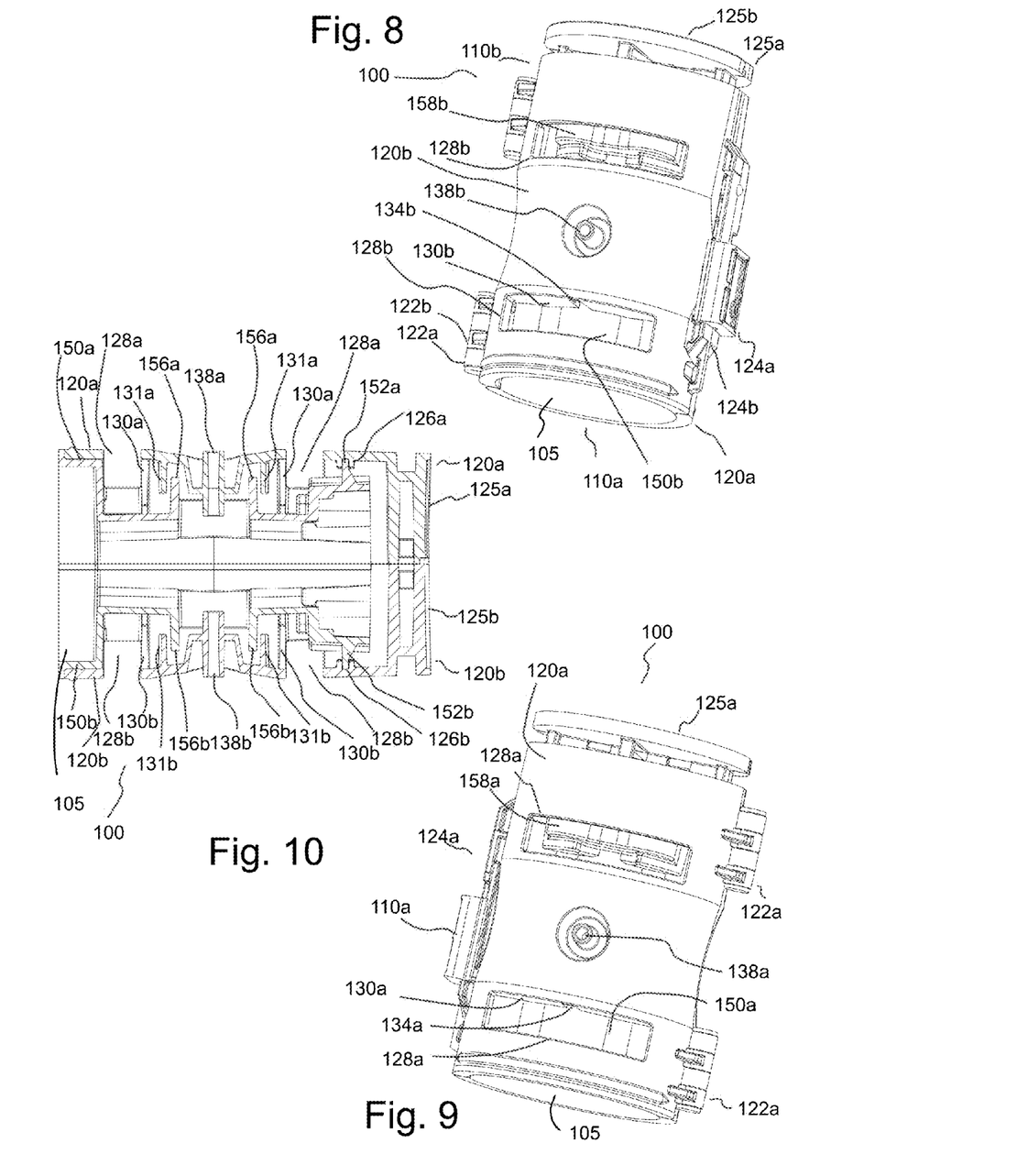
FIG. 8 illustrates another perspective view of the protective enclosure of FIG. 1 in a closed state.
FIG. 9 illustrates another perspective view of the protective enclosure of FIG. 1 in a closed state.
FIG. 10 illustrates a cross-sectional view of the protective enclosure of FIG. 1 in a closed state.
Figure 11:
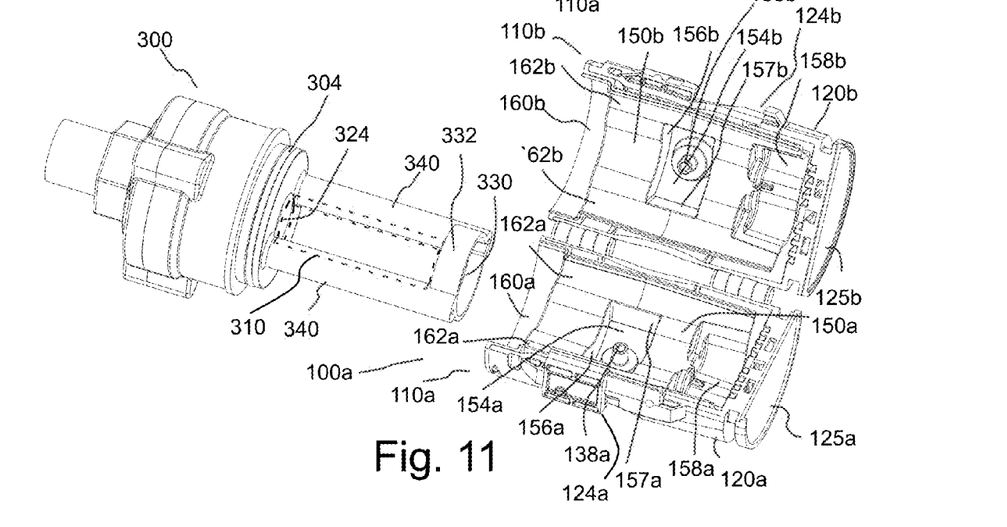
FIG. 11 illustrates a perspective view of the protective enclosure of FIG. 1 in an open state with an embodiment of a sensor adjacent to the protective enclosure.
Figure 12:
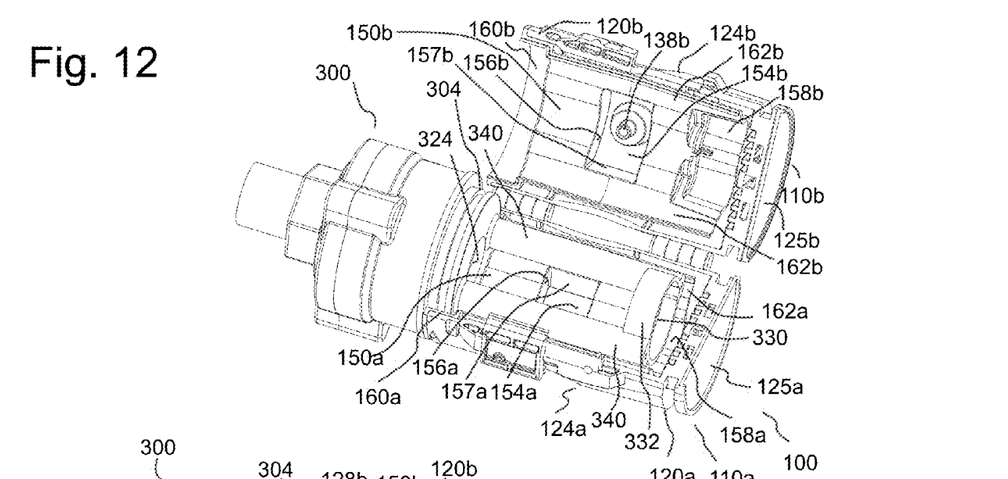
FIG. 12 illustrates a perspective view of the protective enclosure of FIG. 1 in an open state with the sensor positioned therein.
Figure 13:
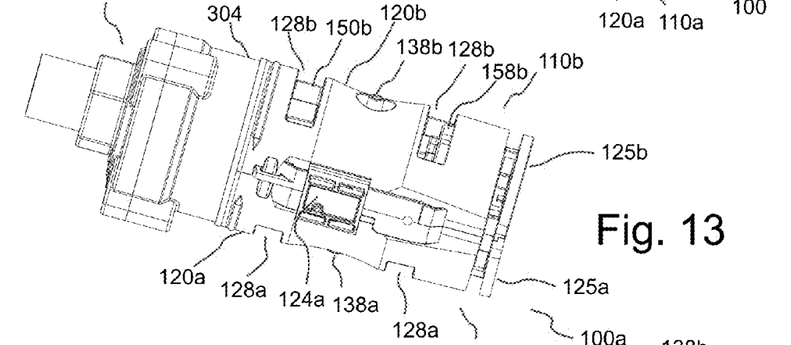
FIG. 13 illustrates a perspective view of the protective enclosure of FIG. 1 in a closed state with the sensor positioned therein.
Figure 14:
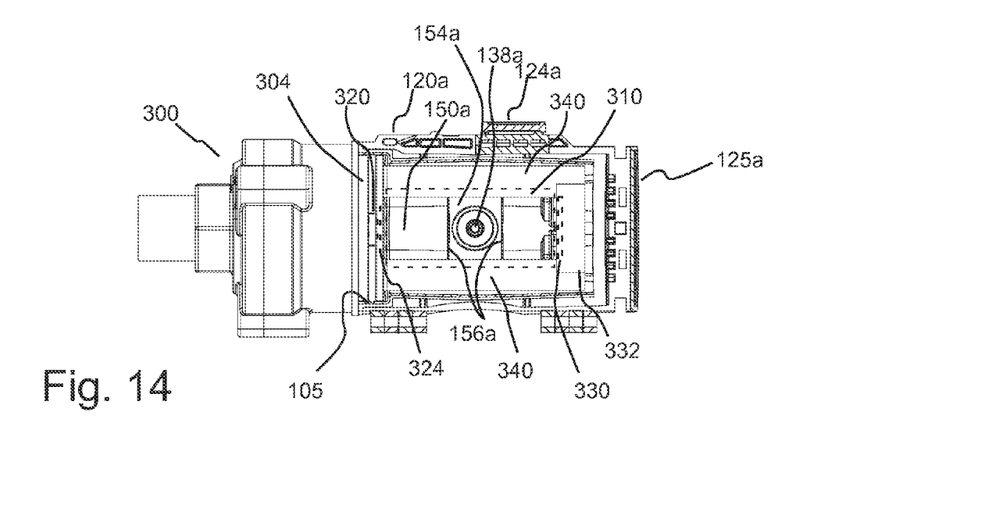
FIG. 14 illustrates a partially cross-sectional view of the protective enclosure of FIG. 1 in a closed state with the sensor positioned therein.
Figure 15:
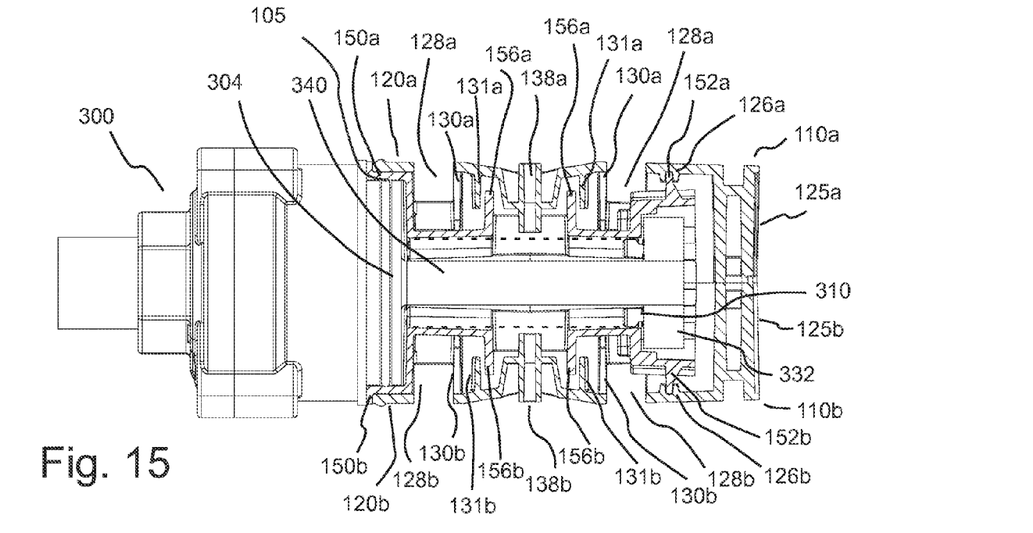
FIG. 15 illustrates another partially cross-sectional view of the protective enclosure of FIG. 1 in a closed state with the sensor positioned therein.
Figure 16:
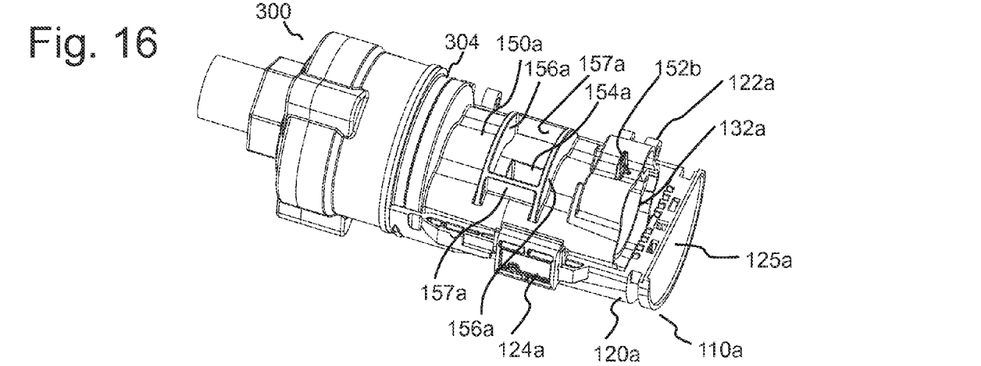
FIG. 16 illustrates a perspective, partially disassembled view of the protective enclosure of FIG. 1 in a closed state with the sensor positioned therein.

Referring, for example, to FIGS. 1 and 2, outer portions 120a and 120b include openings 128a and 128b, respectively, through which gas can enter protective enclosure 100 and water can flow out of protective enclosure 100 when sensor 300 is enclosed therein. Outer portions 120a and 120b further include radially inwardly extending (with reference, for example, to axis A illustrated in FIGS. 6 and 7) deflecting or barrier members 130a and 131a, and deflecting or barrier members 130b and 131b, respectively, that assist in creating an indirect, tortuous or circuitous path between openings 128a and 128b and a volume between barrier members 130a and 130b (which is in fluid connection with the analytical volume of sensor 300). As discussed further below, barrier members 130a, 130b 131a and 131b, in cooperation with deflecting or barrier members of inner portions 150a and 150b, restrict access of, for example, water and/or other liquid contaminants to the analytical volume of sensor 300 and to the operative components of infrared sensor 300. In that regard, the analytical volume of sensor 300 or that volume probed by sensor 300, is located between an infrared light source/sensor system 320 (represented schematically by dashed lines in FIG. 14), which is positioned behind a translucent window 324 within a base 304 of sensor 300, and a mirror system 330. The barrier members of protective enclosure 100 restrict access of, for example, water and/or other liquid contaminants to the analytical volume, to window 324 and/or to mirror system 330. Barrier members 130a and 130b can, for example, include passages or slots 134a and 134b, respectively to allow any water that passes into the volume between barrier members 130a and 130b to drain therefrom and exit protective enclosure 100 via openings 128a or 128b.

Inner portions 150a and 150b include openings 154a and 154b bordered by radially inward extending deflecting or barrier members 156a and 156b. Similar to barrier members 130a, 130b, 131a and 131b, barrier members 156a and 156b extend generally perpendicular to axis A. In the illustrated embodiment, openings 154a and 154b are further bordered by radially inward extending deflecting or barrier members 157a and 157b, which extend between barrier members 156a and 156b, generally parallel to axis A. Upon assembly of inner portions 150a and 150b with outer portions 110a and 110b, barrier members 156a and 156b are positioned between barrier members 131a and 131b respectively. Although gas can readily pass around the extending edges of the barrier members of outer portions 120a and 120b and inner portions 150a and 150b, the indirect, tortuous or circuitous path created thereby provides a significant barrier to passage of, for example, water and other liquid contaminants.

Inner members 150a and 150b can, for example, be formed to correspond relatively closely in dimensions and shape to the dimensions and shape of a portion of sensor 300 encompassed by protective enclosure 100. For example, inner members 150a and 150b can include radially outwardly extending seatings 158a and 158b, respectively, for a mirror support 332 (which supports mirror system 330) of sensor 300 and radially outwardly extending seatings 160a and 160b, respectively, for base section 304 of sensor 300. Likewise, inner members 150a and 150b can, for example, include seatings 162a and 162b conforming to the shape of supports 340, which extend from base 304 of sensor 300 to connect to mirror support 332.

Currently available protective enclosures for use with sensors such as infrared sensors are designed to slide over a front section or portion of such sensors (for example, over the mirror end of such sensor) when the sensor is installed (for example, to extend from a surface) to connect to and encompass the sensor. To enable such protective enclosures to pass over the portion of the sensor to be enclosed by the protective enclosure, an internal volume of the protective enclosure, which is in connection with a rearward opening through which the front section of the sensor passes, must be relatively large with respect to sensor components and/or sensor component size (for example, mirror size). In that regard, for example, the minimum internal radius or internal minimum cross-sectional area along the length of the volume within which the sensor is retained in currently available protective enclosures can be no smaller than the maximum radius or cross-section area of a sensor component over which such a protective covering must pass to be placed in operative connection with the sensor.

On the other hand, the protective enclosures described herein are not so limited. In a number of embodiments, the protective enclosures hereof include at least one section that is movable relative to at least one other section to enable the protective enclosures to be placed in operative connection with a sensor. As, for example, illustrated in FIGS. 7 and 11 through 14, sections 110a and 110b form an opening or seating 105 which encompasses a portion of an installed sensor such as sensor 300 when sections 110a and 110b are in a closed state. In the illustrated embodiment, opening 105 is formed by seatings 160a and 160b to encompass a perimeter of base 304. Protective enclosure 100 can thus be taken from an open state to a closed state to encompass a forward, extending section of sensor 300 including analytical volume 310 within the internal volume of protective enclosure 100 (that is, the free volume within protective enclosure 100 when sensor 300 is encompassed thereby). Opening 105 can, for example, have a greater radius or cross-sectional area than the maximum or average radius or cross-sectional area of an internal volume of protective enclosure 100. Opening or seating 105 can, for example, form a sealing or partially sealing engagement with base 304. Encompassing a section of sensor 300 or another sensor via movable sections of a protective enclosure results in a reduction or minimization of an internal volume of the protective enclosure which is in fluid connection with the analytical volume of the sensor as compared to previously available protective enclosures. Protective enclosures described herein can, for example, include radially outwardly extending seating sections to encompass at least a portion of a radially outwardly extending component of the sensor such that at least a portion of the internal volume within the protective enclosure has a radius or cross-sectional area less than the radius or cross-sectional area of a component of the sensor encompassed by the protective enclosure (for example, less than a maximum (or even a minimum) cross-sectional area of mirror support 332. The reduction or minimization of the internal volume (which is only slightly larger than analytical volume 310 represented schematically in dashed lines in, for example, FIGS. 7 11, 14 and 15) of protective enclosure 100 (which encompasses the analytical volume of sensor 300) enables faster response times for the sensor and improved channeling for water rejection.

The relatively long indirect, tortuous, circuitous or labyrinth pathways created by the barrier members of the protective enclosures and the small internal volume in fluid connection with the sensor analytical volume also provide for the decoupling of the rotational position of the protective enclosures and their response time. As compared to currently available protective enclosures, protective enclosure 100 can, for example, provide reduced sensitivity to orientation. Protective enclosure 100 can, for example, be rotated around axis A to a variety of positions without substantially adversely affecting water resistance and/or response time. Likewise, axis A of protective enclosure 100 can be tilted out of the horizontal plane over a range of positions. Moreover, in a number of embodiments (such as the hinging or "clam shell" design illustrated in FIGS. 1 through 16), the protective enclosures described herein can be installed with one hand and without tooling. The external, installation footprint of the protective enclosures described herein can, for example, be smaller than many currently available protective enclosures. By reducing or minimizing the internal volume in fluid connection with the sensor analytical volume, the volume between the two layers that make up the labyrinth pathway can, for example, be increased without increasing the overall size or footprint of the protective enclosure.

As described above, the sectional design of the protective enclosures described herein allows for a relatively small footprint for installation. For example, there is no need for the user to provide for space beyond the distal end of the sensor to install the protective enclosure. In the case of the representative "clam shell" embodiment of protective enclosure 100, for example, protective enclosure 100 can be readily installed by rotating or pivoting sections 110a and 110b around sensor 300 and clamping sections 110a and 110b into a closed state using closure 124a.

In the illustrated representative embodiment, protective enclosure 100 further includes one or more ports 138a and 138b, formed in outer sections 120a and 120b, for delivery of, for example, a calibration gas to sensor 300. In the illustrated embodiment, ports 138a and 138b extend radially inwardly to be in fluid connection with openings 154a and 154b of inner portions 150a and 150b for delivery of calibration gas to the analytical volume of sensor 300.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of protecting a gas sensor installed in an environment in which gas is to be tested, comprising:
   providing a protective enclosure formed in a plurality of sections, at least a first section of the plurality of sections being movable relative to a second section of the plurality of sections so that the protective enclosure can be placed around at least a portion of the installed sensor;
   placing the first section adjacent the installed sensor while the first section and the second section are in an open state; and
   moving the second section to place the first section and the second section in a closed state in which the first section and the second section encompass the at least a portion of the installed sensor, wherein the second section is movable relative to the first section to enclose at least a portion of the installed sensor comprising an analytical volume of the installed sensor within an internal volume of the protective enclosure.

2. The method of claim 1 wherein the protective enclosure further comprises at least a first opening in the first section via which an analyte gas can enter the internal volume and an indirect pathway between the first opening and the internal volume.

3. The method of claim 2 wherein the first section is moveably connected to the second section via at least one hinged connection.

4. The method of claim 2 wherein the indirect pathway between the first opening and the internal volume is created by at least one barrier member extending from a first outer portion of the first section and at least one barrier member extending from a first inner portion of the first section.

5. A system, comprising:
   an infrared gas sensor; and
   a protective enclosure removably attachable to at least a portion of the sensor; the protective enclosure comprising a plurality of sections, at least a first section of the plurality of sections being movable relative to a second section of the plurality of sections to enclose at least a portion of the sensor comprising an analytical volume of the sensor within an internal volume of the protective enclosure.

6. The system of claim 5 wherein the protective enclosure further comprises at least a first opening in the first section via which an analyte gas can enter the internal volume and an indirect pathway between the first opening and the internal volume.

7. The system of claim 6 wherein the first section is moveably connected to the second section via at least one hinged connection.

8. The system of claim 7 wherein the first section comprises a first outer portion and a first inner portion and the second section comprise a second outer portion and a second inner portion.

9. The system of claim 8 wherein the indirect pathway between the first opening and the internal volume is created by at least one barrier member extending from the first outer portion and at least one barrier member extending from the first inner portion.

10. The system of claim 9 further comprising at least a second opening in the second section via which an analyte gas can enter the internal volume and an indirect pathway between the second opening and the internal volume, the indirect pathway between the second opening and the internal volume being created by at least one barrier member extending from the second outer portion and at least one barrier member extending from the second inner portion.

11. The system of claim 7 wherein a minimum cross-sectional area of the internal volume is less than the cross sectional area of a component of the sensor encompassed by the protective enclosure.

12. The system of claim 11 wherein the sensor comprises a mirror support to which at least one mirror is attached, at least one of the first inner portion and the second inner portion including a seating to seat the mirror support.

13. A protective enclosure for use in connection with a gas sensor installed in an environment in which gas is to be tested; comprising:
   a first section, a second section movable relative to the first section to enclose at least a portion of the installed sensor comprising an analytical volume of the installed sensor within an internal volume of the protective enclosure, at least a first opening in the first section via which an analyte gas can enter the internal volume, and an indirect pathway between the first opening and the internal volume created by cooperation of the first section and the second section.

14. The protective enclosure of claim 13 wherein the first section is moveably connected to the second section via at least one hinged connection.

15. The protective enclosure of claim 14 wherein the first section comprises a first outer portion and a first inner portion and the second section comprise a second outer portion and a second inner portion.

16. The protective enclosure of claim 15 wherein the indirect pathway is created by at least one barrier member extending from the first outer portion and at least one barrier member extending from the first inner portion.

17. The protective enclosure of claim 16 further comprising at least a second opening in the second section via which an analyte gas can enter the internal volume and an indirect pathway between the second opening and the internal volume, the indirect pathway between the second opening and the internal volume being created by at least one barrier member extending from the second outer portion and at least one barrier member extending from the second inner portion.

18. The protective enclosure of claim 14 wherein a minimum cross-sectional area of the internal volume is less than the cross sectional area of a component of the sensor encompassed by the protective enclosure.

19. The protective enclosure of claim 18 wherein the sensor is an infrared sensor comprising a mirror support to which at least one mirror is attached, at least one of the first inner portion and the second inner portion including a seating to seat the mirror support.

\* \* \* \* \*